18-217 SR
IP8502 DR RE 22,763
June 11, 1946. W. F. CLARK Re 22,763
MATTRESS FOR TREATING HUMAN BODY AILMENTS BY HEAT THERAPY Orig. 2376,902
Original Filed Feb. 27, 1943 2 Sheets-Sheet 1.
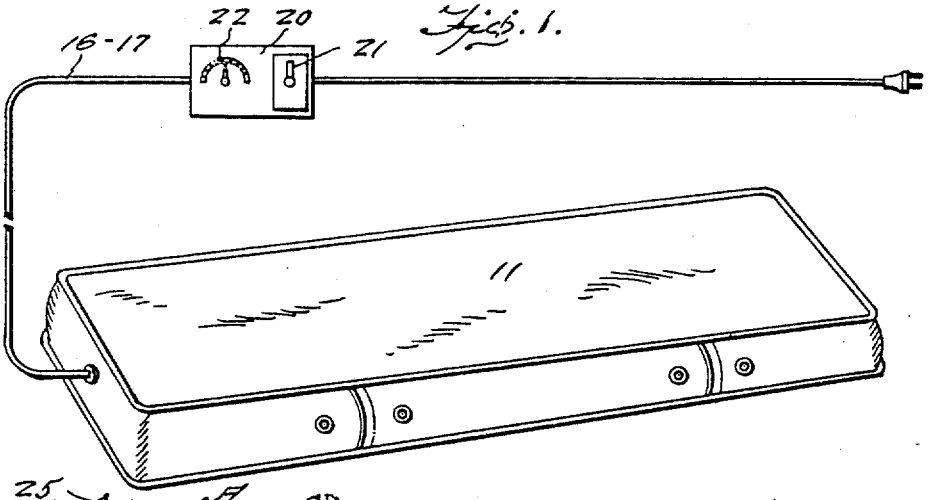
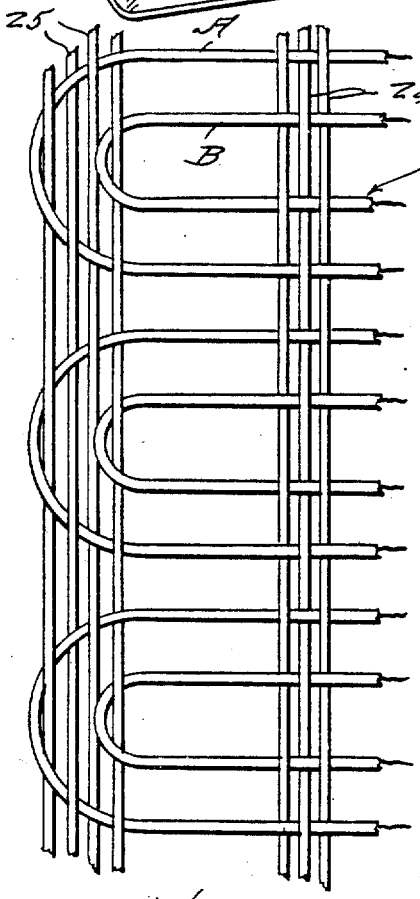
Fig. 4.
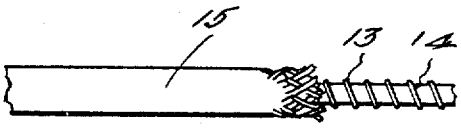
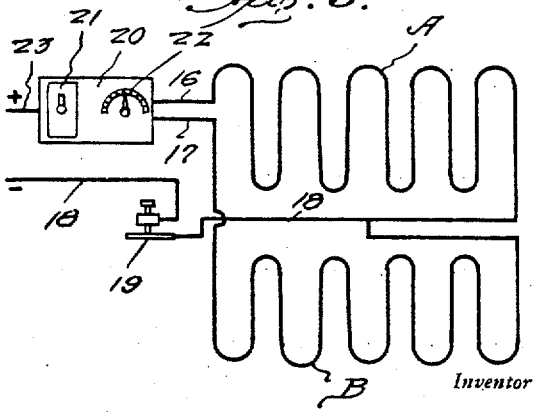
Inventor
Warren F. Clark
By Clarence A. O'Brien and Harvey B. Jacobson
Attorneys June 11, 1946. W. F. CLARK Re 22,763
MATTRESS FOR TREATING HUMAN BODY AILMENTS BY HEAT THERAPY
Original Filed Feb. 27, 1943 2 Sheets-Sheet 2
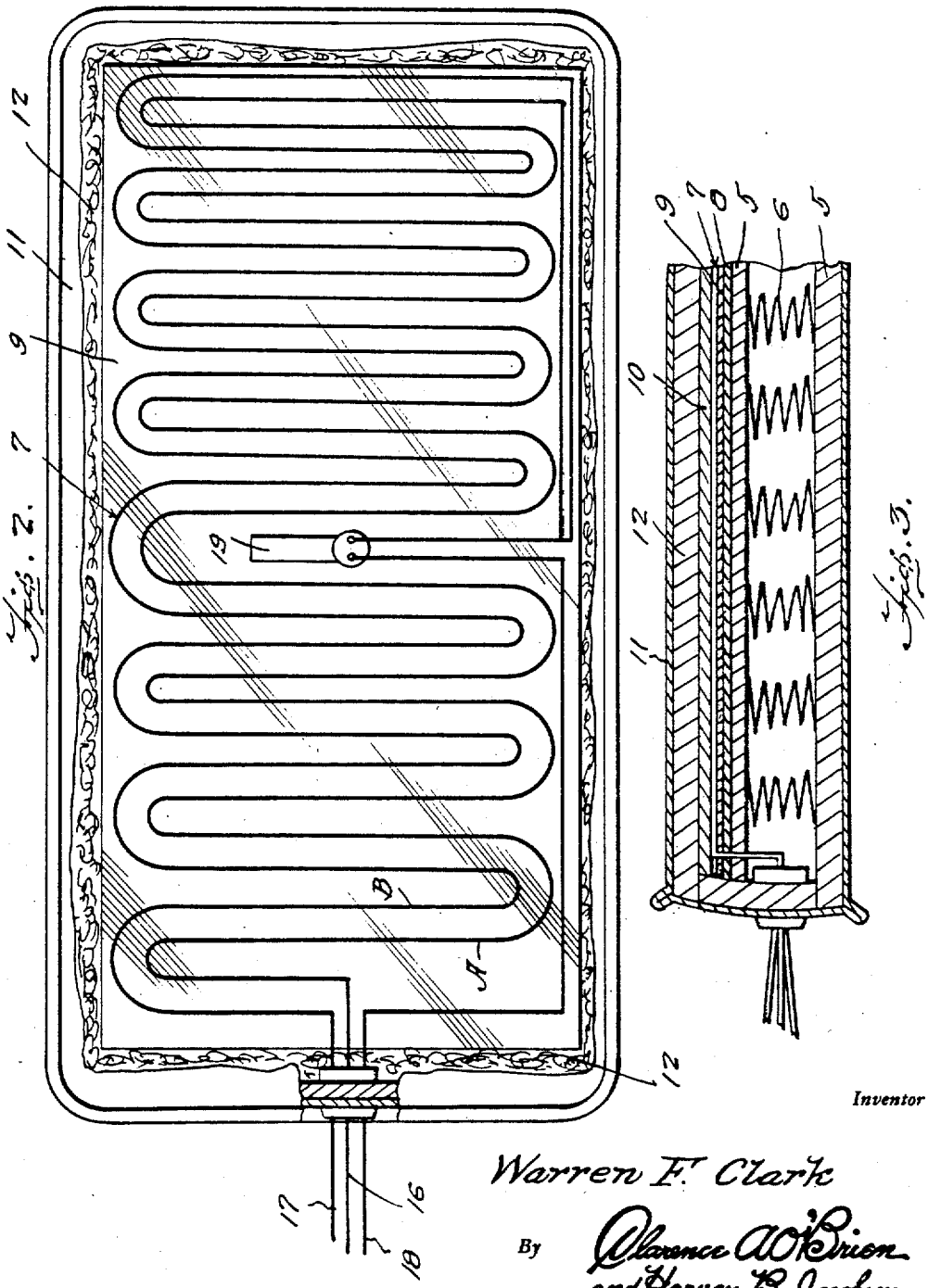
Inventor
Warren F. Clark
By Clarence A. O'Brien and Harvey B. Jacobson
Attorneys Reissued June 11, 1946

Re. 22,763

UNITED STATES PATENT OFFICE 22,763

MATTRESS FOR TREATING HUMAN BODY AILMENTS BY HEAT THERAPY

Warren F. Clark, Nashville, Tenn.

Original No. 2,376,902, dated May 29, 1945, Serial No. 477,433, February 27, 1943. Application for reissue October 4, 1945, Serial No. 620,341

8 Claims. (Cl. 219—46)

The present invention appertains to new and useful improvements in the art of heat therapy and more particularly to a novel electric heat producing mattress for treating various human body ailments.

The principal object of the present invention is to provide a mattress for treating patients by heat therapy, in which the heat is regulated and controlled to a precise degree and in such a manner as to promote the circulation of blood of the patient.

Another important object of the invention is to provide an electric mattress of the character stated which is substantially fool-proof in all respects.

Still another important object of the invention is to provide a structure in the form of a mattress upon which a person can lie under various conditions and be subject to a treatment of heat therapy.

Various other important objects and advantages of the invention will become apparent to the reader of the following description.

In the drawings:

Figure 1 is a perspective view of the apparatus.

Figure 2 is a top plan view with a top portion of the mattress removed and showing diagrammatically the electrical wiring.

Figure 3 is a fragmentary longitudinal sectional view through the mattress.

Figure 4 is a fragmentary diagrammatic view showing the manner in which the heat wires are woven in place.

Figure 5 is a fragmentary side elevational view of one of the heat wires.

Figure 6 is a diagrammatic view showing the electrical connection between the electrical devices involved.

Referring to the drawings wherein like numerals designate like parts, it can be seen that the mattress preferably includes top and bottom walls 5, 5 between which springs 6 are located. Numeral 7 denotes a heating unit between which and the top wall 5 an asbestos sheet 8 is located, having on its top side, a sheet 9 of aluminum foil, this for the purpose of radiating heat upwardly.

A sheet of felt 10 is placed over the heating unit 7 and the entire structure is provided with a case or covering 11 of some suitable material (preferably waterproof) and inside of which is suitable upholstery 12.

The heating unit 7 is made up of resistant wires 13 wrapped around cores 14 of asbestos or some like material and over this is preferably a braided or otherwise formed covering 15.

An important factor of the present invention is that the heating unit is actually woven in place, as shown in Figure 4 in order that the heating wires will be equally distributed in the mattress and to the end that there will be no hot spots tending to reduce the efficiency of the mattress.

As shown in Figure 6 and further shown in Figure 2, the unit includes two circuits A and B, in parallel relation. These circuits A and B have current feed conductors 16, 17 and a single return wire 18 by way of a thermostatic unit 19 which is centrally located in the mattress as shown in Figure 2 so as to regulate the heat and hold the same to the desired degree.

One circuit, for instance, the circuit A will be a low heat producing circuit, while the other circuit B will be a high heat producing circuit, these circuits being connected up with different valued outputs from a control box 20 which is provided with a switch 21 whereby one or the other, or both of the circuits A, B can be utilized and a rheostat 22 for regulating the input of current from a supply line 23.

It can be seen, that the wires of the two circuits A, B are arranged back and forth across the mattress and interwoven with spacing ties 24 and woven selvage 25, the curves of the wires being interwoven or meshed in the selvage 25 as well as the spacing ties 24.

It will be observed in Figure 2, that the wire of one circuit follows in parallel relation the wire of the other circuit, and at the foot portion of the mattress the flights of the resistance wires are closer together so that there will be a greater length of these wires at the foot portion of the mattress. Thus it can be seen that there will be a substantially higher degree of heat at the foot portion of the mattress than at the head portion, and the heat being applied to the foot and leg portions of the patient will serve to promote a blood circulation highly beneficial when the patient is subject to heat therapy treatment.

While the foregoing specification sets forth the invention in specific terms, it is to be understood that numerous changes in the shape, size and materials may be resorted to without departing from the spirit and scope of the invention as claimed hereinafter.

Having described the invention, what is claimed as new is:

1. A heated mattress comprising a hollow elongated rectangular body of upholstering material having a closed chamber therein extending substantially from side to side and end to end of the same, a covering for said body, springs arranged in the lower portion of said chamber, an asbestos sheet supported on said springs, a sheet of aluminum foil disposed on said asbestos sheet, a heating unit disposed on said sheet of foil and embodying a mat-like structure in which a heating element is woven, said sheets and said heating unit substantially corresponding in length and width to the chamber, a sheet of felt disposed on said heating unit, and means to connect said heating element to a source of electricity.

2. A heated mattress comprising a hollow elongated rectangular body of upholstering material having a closed chamber therein extending substantially from side to side and end to end of the same, a covering for said body, springs arranged in the lower portion of said chamber, an asbestos sheet supported on said springs, a sheet of aluminum foil disposed on said asbestos sheet, a heating unit disposed on said sheet of foil and embodying a mat-like structure in which a heating element is woven, said sheets and said heating unit substantially corresponding in length and width to the chamber, a sheet of felt disposed on said heating unit, and means to connect said heating element to a source of electricity, said heating element including a pair of spaced parallel resistance wires extending back and forth transversely of the mattress in zig-zag formation, the flights of said wires being closer together at the foot portion of the mattress than at the head portion thereof.

3. A heated mattress comprising an elongated rectangular body of upholstering material, and a covering for said body, an insulating sheet supported on said body, a sheet of metallic foil disposed on said insulating sheet, a heating unit disposed on said sheet of foil and separated from the insulating sheet by the foil, said heating unit embodying a mat-like structure in which a heating element is woven, the sheets and the heating unit substantially corresponding in length and width to the rectangular body of the mattress, a sheet of felt disposed over the heating unit, and means to connect said heating element to a source of electricity.

4. A heated mattress comprising an elongated rectangular body of upholstering material, and a covering for said body, an insulating sheet supported on said body, a sheet of metallic foil disposed on said insulating sheet, a heating unit disposed on said sheet of foil and separated from the insulating sheet by the foil, said heating unit embodying a mat-like structure in which a heating element is woven, the sheets and the heating unit substantially corresponding in length and width to the rectangular body of the mattress, a sheet of felt disposed over the heating unit, means to connect said heating element to a source of electricity, said heating element including a pair of spaced parallel resistance wires extending back and forth transversely of the mattress in zig-zag formation, the flights of said wires being closer together at the foot portion of the mattress than at the head portion thereof.

5. A mattress having a head end and a foot end, and comprising a cushion approximating the size of the mattress, a pair of elongated resistance heater wires entering an end of the cushion and both directed sinuously in spaced substantial parallelism from side to side of the cushion throughout the length thereof, to heat both the head end and the foot end of the mattress, the flights of the wires at the foot end being more closely spaced than those at the head end, a waterproof cover overlying the heater wires and the cushion, and means for electrically connecting the opposite ends of said resistance heater wires in circuit with a source of electricity.

6. A mattress having a head end and a foot end, and comprising a cushion approximating the size of the mattress, a pair of elongated resistance heater wires entering an end of the cushion and both directed sinuously in spaced substantial parallelism from side to side of the cushion throughout the length thereof, to heat both the head end and the foot end of the mattress, the flights of the wires at the foot end being more closely spaced than those at the head end, a waterproof cover overlying the heater wires and the cushion, means for electrically connecting the opposite ends of said resistance heater wires in circuit with a source of electricity, and means electrically connected in the circuit of each heater wire for controlling the heat output of said wires individually.

7. A mattress having a head end and a foot end, and comprising a cushion approximating the size of the mattress, a pair of continuous and coextensive resistance heater wires entering an end of the cushion and both directed in loop form sinuously in spaced substantial parallelism with the flights between successive loops extending from side to side of the cushion throughout the length thereof, to heat both the head end and the foot end of the mattress, the flights of the wires at the foot end being more closely spaced than those at the head end, a waterproof cover overlying the heater wires and the cushion, and means for electrically connecting the opposite ends of said resistance heater wires in circuit with a source of electricity.

8. A mattress having a head end and a foot end, and comprising a cushion approximating the size of the mattress, a pair of continuous and coextensive resistance heater wires entering an end of the cushion and both directed in loop form sinuously in spaced substantial parallelism with the flights between successive loops extending from side to side of the cushion throughout the length thereof, to heat both the head end and the foot end of the mattress, the flights of the wires at the foot end being more closely spaced than those at the head end, means for electrically connecting the opposite ends of said resistance heater wires in circuit with a source of electricity, and means electrically connected in the circuit of each heater wire for controlling the heat output of said wires individually.

WARREN F. CLARK.

1837117 219-46
1989582 "
2138745 "
2215042 "
1994758 "

1833761 219-46X
1391762 "
2265335 "